(12) United States Patent
Taylor et al.

(10) Patent No.: US 7,791,044 B1
(45) Date of Patent: Sep. 7, 2010

(54) STATION FOR DISINFECTING PUBLICLY-USED EQUIPMENT

(75) Inventors: Thomas L. Taylor, Yorba Linda, CA (US); Pat Hilt, Rancho Cucamonga, CA (US)

(73) Assignee: Yorba Linda Enterprises, LLC, Yorba Linda, CA (US)

( * ) Notice: Subject to any disclaimer, the term of this patent is extended or adjusted under 35 U.S.C. 154(b) by 0 days.

(21) Appl. No.: 12/755,295

(22) Filed: Apr. 6, 2010

Related U.S. Application Data (60) Provisional application No. 61/247,361, filed on Sep. 30, 2009.

(51) Int. Cl.
*A61L 2/10* (2006.01)
(52) U.S. Cl. ............... 250/455.11; 250/453.11; 250/493.1; 250/504 R; 422/1; 422/22; 422/24
(58) Field of Classification Search ............ 422/1, 422/7, 20, 21, 22, 24; 250/428, 431, 432 R, 250/433, 436, 453.11, 454.11, 455.11, 492.1, 250/493.1, 494.1, 503.1, 504 R
See application file for complete search history.

(56) References Cited

U.S. PATENT DOCUMENTS

| | | | |
|---|---|---|---|
| 5,597,597 A * | 1/1997 | Newman | 426/248 |
| 5,958,336 A | 9/1999 | Duarte | |
| 6,649,921 B1 | 11/2003 | Cekic et al. | |
| 2004/0052702 A1* | 3/2004 | Shuman et al. | 422/208 |
| 2006/0186358 A1* | 8/2006 | Couvillion | 250/504 R |
| 2007/0012340 A1 | 1/2007 | Jones et al. | |
| 2010/0007492 A1* | 1/2010 | Ressler et al. | 340/540 |

FOREIGN PATENT DOCUMENTS

EP 0755271 1/2002

* cited by examiner

*Primary Examiner*—Jack I Berman
*Assistant Examiner*—Nicole Ippolito Rausch
(74) *Attorney, Agent, or Firm*—Fish & Associates (57) ABSTRACT

A device for disinfecting publicly-used equipment includes a plurality of reflective units disposed along the interior of each wall of the device. Each of the reflective units can include a reflective back section and at least three reflective sections disposed about the reflective back section. UV lamps can be disposed to extend along the walls, and at partially disposed adjacent to a one or more reflective back sections of the reflective units. The UV lamps together with the reflective units collectively direct sufficient UV light on the equipment such that the equipment can be disinfected. The walls and ceiling of the device define a tunnel into which the equipment to be disinfected is inserted. Optionally, the device can include a door to prevent children and others from entering the tunnel while the UV lamps are illuminated.

16 Claims, 7 Drawing Sheets

STATION FOR DISINFECTING PUBLICLY-USED EQUIPMENT

This application claims priority to our copending U.S. provisional application with the Ser. No. 61/247,361 which was filed Sep. 30, 2009, and which is incorporated by reference herein.

FIELD OF THE INVENTION

The field of the invention is disinfection devices.

BACKGROUND

It is known to utilize ultraviolet ("UV") light to sterilize needles, catheters and other medical devices, to thereby reduce the risk of infection to patients. Such practice has also been applied to food, air, water, and other items, although in these other instances the effect is usually to disinfect rather than to sterilize. UV emitters can be stationary or portable, and can range in size from very large devices through which entire pallets of material can be processed, to small hand-held wands for home use.

Surprisingly, existing UV emitter stations are impractical to disinfect publicly used equipment, despite the number of microorganisms that has been found to exist on surfaces including *enteroccocus faecalis, escherichia coli, legionella pneumophila, legionella bozemanii, salmonella enteritidis, salmonela paratyphi* (enteric fever), *salmonella typhosa* (typhoid fever), *salmonella typhimurium, staphylococcus aerius, e. coli*, and rotavirus. For example, known handheld UV emitters have insufficient power to conveniently disinfect a shopping cart, let alone dozens of carts. As a result, the present efforts at grocery stores, amusement parks and so forth are directed to annual or semi-annual spray washing, which may or may not include application of antiseptic chemicals. This is problematic as such dirty equipment exposes the public to harmful bacteria and other microorganisms.

In an attempt to reduce the public's exposure, stores and other locations provide sanitary wipes that can be used by individual customers to disinfect publicly-used equipment. However, each wipe is only minimally effective, and wipes are impractical for cleaning more than a small portion of a piece of equipment.

U.S. Patent Appl. No. 2007/0012340 to Jones discusses a system for cleaning shopping carts and other reusable items that includes a plurality of steps, such as rinsing and drying the carts, and then subjecting the carts to pulses of UV light. Although the Jones system could be useful in cleaning dirty carts, the system is disadvantageous for simply disinfecting carts because the many components have large energy requirements, and the overly complex system will likely lead to higher maintenance costs. Jones and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

U.S. Patent Appl. No. 2006/0186358 to Couvillion discusses a disinfecting system that uses a single UV light source to disinfect shopping carts. Although the Couvillion system reduces energy costs compared with the Jones system by using only a UV light source, the Couvillion device fails to sufficiently disinfect an entire cart due to the minimal UV light source mounted along the ceiling.

It is known to use a plurality of UV lights to decontaminate objects. For example, U.S. Patent Appl. No. 5958336 to Duarte and European Patent No. 0755271 to Shodeen discuss surface sterilization devices that can utilize UV light to decontaminate items as they are conveyed from a contaminated area to a clean area. Although the devices apparently suffice in decontaminating the objects, the high number of UV lamps used will increase usage and maintenance costs of the device, and the V-shape configuration of the reflectors would likely be insufficient to disinfect a non-moving object.

U.S. Pat. No. 6,649,921 to Cekic et al. discusses positioning a UV light within a reflective trough that has reflective sections disposed about the trough in order to provide substantially two-dimensional uniform radiation of a planar surface. However, the Cekic apparatus is configured to direct UV radiation to a planar surface at a set distance, and would likely be insufficient to irradiate non-planar surfaces at varying distances from the UV light source.

Thus, there is still a need for improved disinfection methods and apparatus for use on publicly-used equipment.

SUMMARY OF THE INVENTION

The inventive subject matter provides apparatus, systems and methods in which a device for disinfecting publicly-used equipment includes a housing that defines a tunnel having a vertical cross-section that is rectangular, or an inverted "U" shape. However, other shapes are also contemplated for the tunnel, including for example, those having vertical cross-sections that are triangles, polygons, and so forth. The tunnel can have at least one opening into which equipment can be inserted and irradiated. The height of the opening can vary depending on the equipment to be disinfected. In some contemplated embodiments, the equipment can be a shopping cart, and the opening can have a height of at least 1 meter, and more preferably, at least 1.25 meters.

As used herein, the "equipment" being contemplated are portable carriers used by the public outside the control and/or view of the carriers' owners, and includes, for example, shopping carts, shopping baskets, and strollers. As used herein, the term "reflective unit" means a collection of reflective sections that together reflect at least 60% of light having a frequency between 100 nm to 290 nm. As used herein, the term "extend [ing] along the wall" means extending generally within 5 cm of the wall.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Irradiation is preferably performed by UV lamps, which are advantageously disposed to irradiate the equipment without significantly risking irradiation of customers or operations personnel. Two or more UV lamps are preferably disposed within the tunnel such that a majority of the external surfaces of the equipment are blanketed with the UV light or other radiation. The emitters are preferably oriented to maximize the exposure of equipment within the tunnel, while minimizing the exposure of persons or animals outside the tunnel. The UV lamps can extend along the walls of the housing, as well as the ceiling. It is preferred that at least one of the UV lamps provides an UV light intensity of at least 100 $\mu W/cm2$ of UV light at 1 meter from the UV lamp. In preferred embodiments, the lamps are distanced from the wall by at least 5 cm.

The dose of UV light corresponds to the UV light intensity as a function of time. Dose response levels are unique to each microorganism. Additionally, different wavelengths of UV light have different inactivation rates depending on the microorganism. However, for most microorganisms the peak inactivation wavelength is at or about 260 nanometers (nm). Mercury lamps produce UV light very efficiently at 254 nm and therefore this wavelength has become the standard wavelength in disinfection systems.

The term "disinfect" and "sanitize" are used herein to reflect the expectation that bacterial count will be substantially reduced on irradiated equipment, but not completely eliminated as would be the case with sterilization. As used herein, the phrase "angled off horizontal" means having at least 3 cm$^2$ of top surface that is more than 10° off horizontal. Likewise, the phrase "disposed off normal" means having at least 3 cm$^2$ of top surface that is more than 10° off normal. As used herein, the terms "generally horizontal" and "generally vertical" mean within 10° of a vertical or horizontal axis, respectively, with respect to the device.

The housing can have at least first and second walls, with each wall having a plurality of reflective units. This is advantageous as the reflective units are each designed to direct the UV light from the UV lamps toward the equipment disposed within the tunnel to thereby provide a more uniform distribution of UV light on the equipment's surface.

Each reflective unit preferably has a back section that is reflective, and at least three reflective sections disposed off normal with respect to the back section. In this manner, a recess is created into which one or more UV lamps can be inserted, which advantageously allows more of the UV light to be directed at the equipment. It is contemplated that viewed from the front, the reflective backing could have a triangular shape, a square or rectangular shape, a pentagonal, hexagonal, or any other commercially viable shapes. Of course, depending on the shape of the reflective backing, the shape and number of reflective sections will likely vary. The reflective back section and reflective sections could have a flat, dimpled, bumpy, or other commercially suitable configuration, and such configuration will likely depend on the size and dimension of the housing, and the equipment to be irradiated.

In some contemplated embodiments, the housing can include one or more doors that may be electronically and/or manually operated. The door can be hinged to the housing, can be a roll-up door, or have any other commercially suitable configurations. Optionally, the door can include a window configured to filter UV light, such that a user could view the equipment being disinfected without the associated risks from exposure to UV light. The door preferably is sized and dimensioned to effectively cover the opening, and has a surface area of at least 1 m$^2$.

Contemplated devices could optionally include a conveyor system that automatically feeds the equipment through the tunnel, or into and out from the tunnel. Such systems could include, for example, conveyor belts, tracks, and/or combinations thereof. Alternatively, the equipment could be manually fed or automatically pushed such as by a cart mover.

Guide rails can be installed along the floor or the device, or slightly above the floor, to guide the wheels of wheeled equipment. In addition, the device can have a slanted floor that declines toward a back of the device, such that equipment is encouraged to remain inserted within the device.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
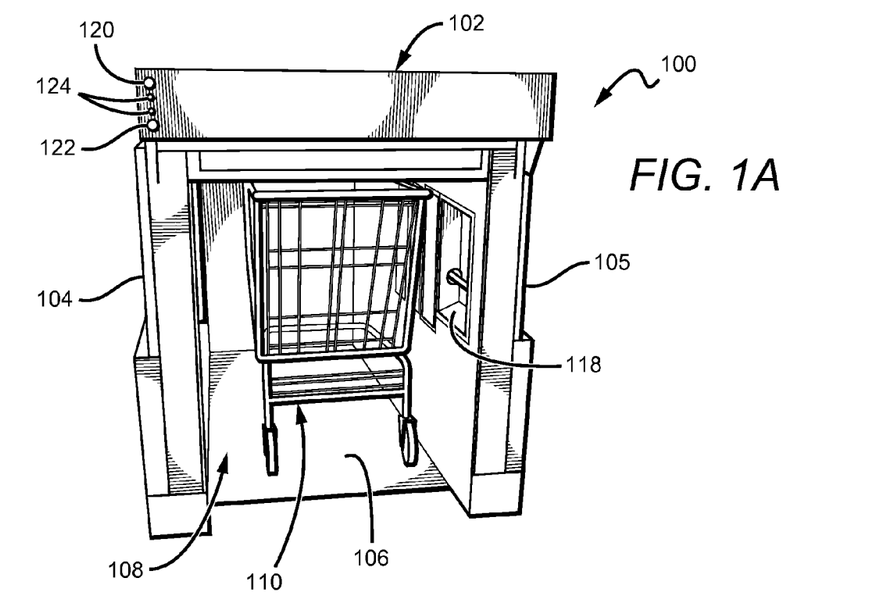
FIG. 1A is a front perspective view of a device for disinfecting publicly-used equipment.
Figure 1B:
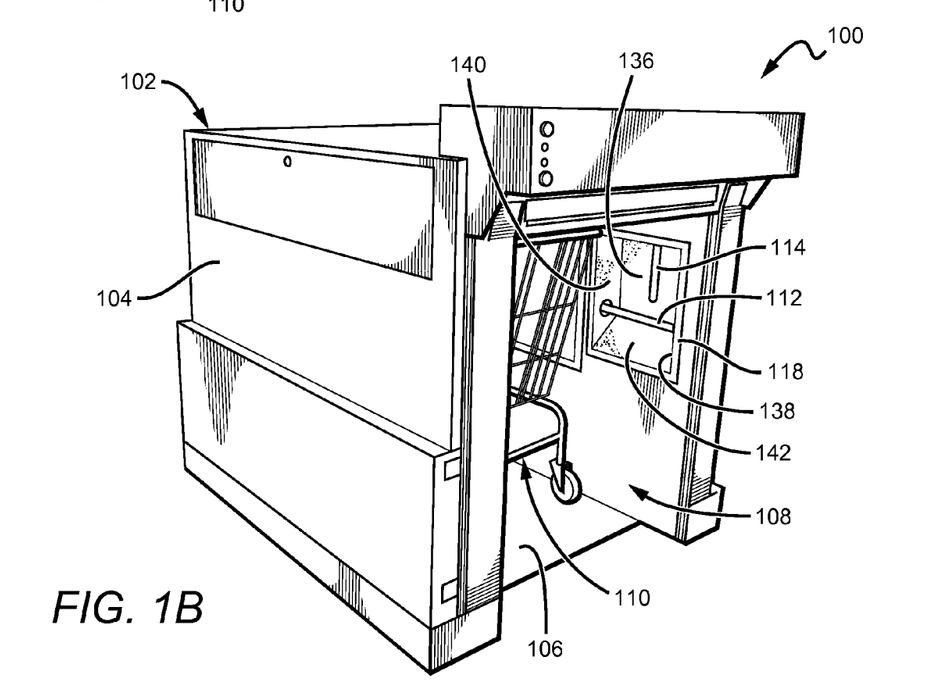
FIG. 1B is a side perspective view of the device of FIG. 1A.
Figure 1C:
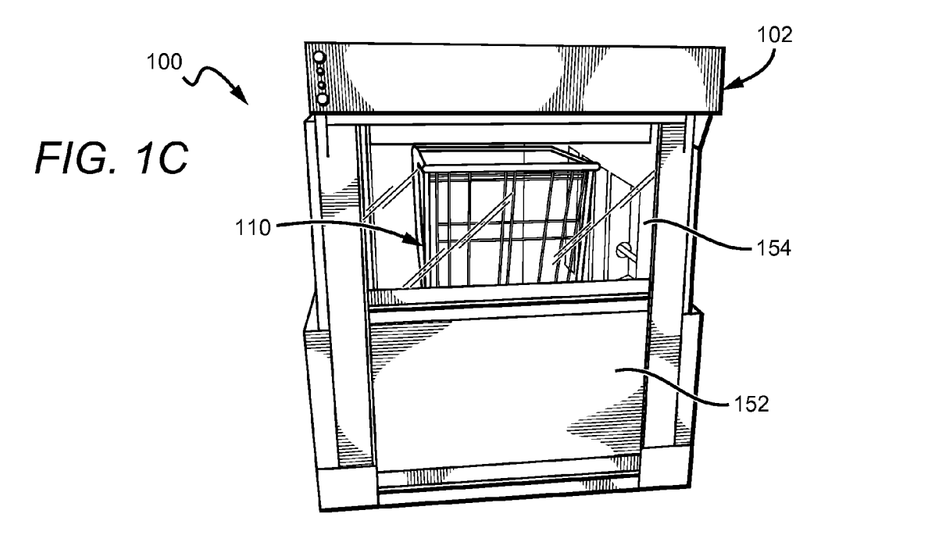
FIG. 1C is a front perspective view of the device of FIG. 1A with a closed door.

In FIGS. 1A-1C, a device 100 is shown that can be used to disinfect publicly-used equipment 110. Although a shopping cart is shown, it is contemplated that the device 100 could be configured to disinfect other publicly-used equipment including, for example, wheel chairs, strollers, and other sizes of shopping carts. Device 100 can include a housing 102 that has first 104 and second walls 105 coupled to a ceiling (not shown). The housing 102 preferably defines a tunnel 106 having a vertical cross-section that is preferably rectangular or an inverted "U" shape. However, other shapes are also contemplated including, for example, triangles, polygons, and so forth. Contemplated devices 100 can be mobile, or mounted to a building or to the ground, for example.

The tunnel 106 can have an opening 108 through which the equipment 110 can be inserted into the tunnel 106. The tunnel 106 can also have a second opening (not shown) through which the equipment 110 can be removed. Alternatively, the equipment 110 can be removed from the tunnel 106 through opening 108. All commercially viable sizes are contemplated for the tunnel 106, and especially those measuring at least 1 m, more preferably, at least 1.2 m, and still more preferably, at least 1.25 m in height to accommodate standard sized grocery shopping carts, wheel chairs, and strollers. The sizes and dimensions of opening 108 and tunnel 106 can vary, however, from installation to installation depending on the equipment 110 to be disinfected. Preferred openings have an area of at least 300 in$^2$. The tunnel 106 can optionally include one or more access openings shown in FIG. 3, such that operators could dislodge jammed carts, replace UV bulbs, and perform other maintenance tasks.

A plurality of reflective units 118 can be coupled to the each of the walls 104 and 105, and in some contemplated embodiments, can be coupled to a ceiling or an optional back wall of the device 100. The reflective units 118 advantageously are disposed about one or more UV lamps such that UV light is redirected toward the equipment, which can thereby reduce the number, size, and/or wattage of the UV lamps required compared with systems of the prior art. As shown in FIG. 1B, the reflective units 118 can include a back section 136, and at least three reflective sections 138, 140, and 142 each of which can be disposed off normal with respect to the back section 136. This is advantageous over the prior art, as the reflective sections direct light in every direction rather than only up and down or left and right. In this manner, the UV intensities on various areas of the equipment can have a greater consistency, requiring less UV bulbs and/or a shorter exposure to the UV light to disinfect the equipment.

In alternative embodiments, the reflective unit could include three sections, or five or more sections. An exemplary embodiment of a reflective unit with three sections is shown in FIG. 10. The reflective units can be composed of one or more commercially suitable materials, including, for example, mirrors, powder-coated and other metal sheets, and Pebbletone™ and Hammertone™ finishes.

First and second UV lamps 112 and 114 can be disposed to extend along the wall 104, and adjacent to the reflective unit 118. In some contemplated embodiments, the first and second UV lamps 112 and 114 can be disposed perpendicularly to each other. Although not shown, additional UV lamps can be disposed along the first wall 104, along the second wall 105, and/or along the ceiling. The specific number, size, and orientations of each of the UV lamps will likely vary depending on the size and type of UV lamp(s) used, the equipment to be disinfected, and the sizes and dimensions of the tunnel and housing.

The UV lamps 112 and 114 can be disposed in any suitable locations and oriented such that equipment 110 within the tunnel 106 is exposed to adequate amounts of UV radiation to disinfect the equipment. It is preferred that the UV lamps 112 and 114 are at least partially disposed within recesses formed from the reflective units 118, which advantageously increases the amount of UV light directed toward the equipment 110, and can also significantly reduce the amount of UV light directed toward opening 108.

Each of the UV lamps 112 and 114 preferably has dual bulbs, although the number of bulbs could be varied. The UV lamps 112 and 114 can produce ultraviolet light, and preferably produce UVc light having a wavelength between 100-290 nm. However, all commercially suitable radiation that disinfects equipment is contemplated including, for example, UVa, UVb, and other wavelengths of UV light. Although the UV lamps are shown having elongated bulbs, it is contemplated that other commercially suitable sources of UV light could be used. A currently preferred UV emitter is a 36 Watt UV bulb by Phillips that produces UV light having a wavelength of 254 nm. Preferred UV lamps produce at least 30 watts of UV light, and at least 75% of which is in the UVc range. In addition, preferred UV lamps produce UV light at an intensity at least 100 µW/cm2 of UV light at 1 meter.

The device 100 can also include a power switch 120 having "on" and "off" positions, which assists in preventing unauthorized use of the device 100 by cutting power to the device 100 unless the switch is in the "on" position. Although the power switch 120 is shown as a key lock, the power switch 120 could alternatively be a keypad, a flip switch, or other commercially suitable configuration(s). Once the power switch is in the "on" position, a user can activate the device 100 by depressing actuating button 122. One or more lights 124 can be illuminated to quickly apprise the user of the status of the device 100. For example, a red light might be illuminated to show that the device 100 is currently in use, and a green light might be illuminated when the device 100 is ready for use. However, the specific triggers for each of the lights 124 can be varied depending on the user's needs.

As shown in FIG. 1C, the device 100 can optionally include a door 152 that can be used to effectively close opening 108. The door 152 is very beneficial as it prevents children, animals, and others from entering into the tunnel 106 while UV lamps 112 and 114 are illuminated. Thus, the UV light is prevented from potentially harming people and animals. Door 152 can include a window 154 that is configured to filter the UV light. This advantageously allows a user to view the equipment 110 as the device 100 is being operated, while preventing the UV light from harming the user. Although door 152 is shown as a roll-up door, it is contemplated that the door 152 could alternatively be a hinged door or any other commercially suitable configuration(s). Door 152 can be electrically operated by an opener. Alternatively or additionally, door 152 could be manually operated.

Figure 2A:
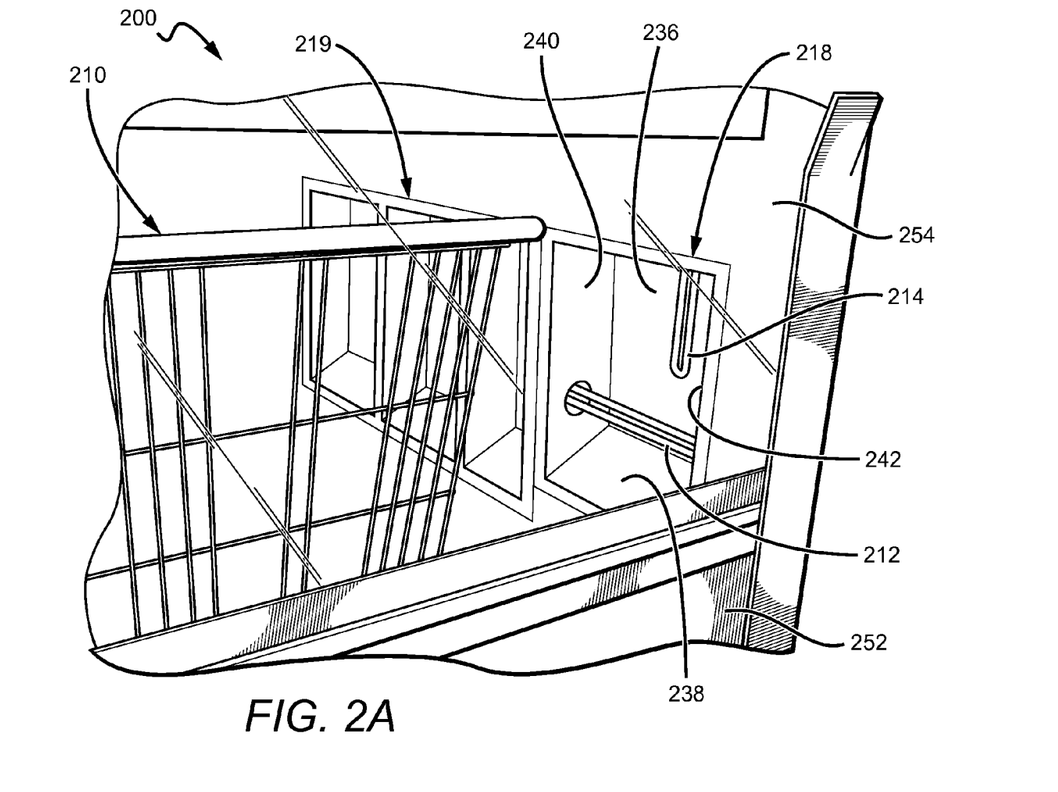
FIG. 2A is a close-up view of an activated device.
Figure 2B:
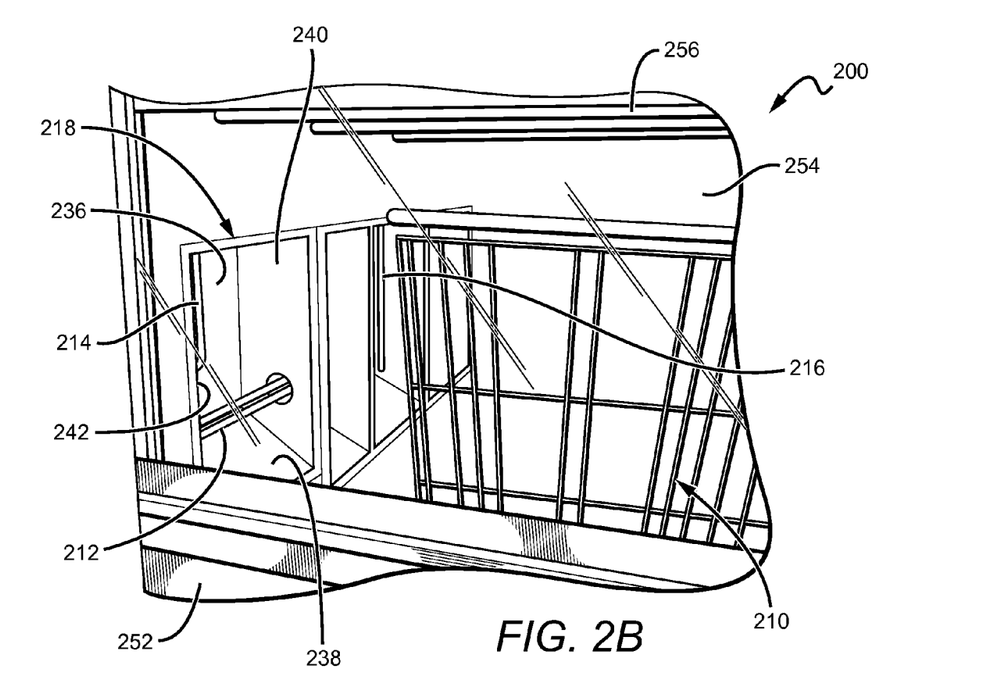
FIG. 2B is an alternate view of the activated device of FIG. 2A.

FIGS. 2A-2B illustrates another embodiment of a device 200 having a roll-up door 252 with a window 254 that is configured to allow a user to view within the tunnel 206 while the device 100 is operating by filtering the UV light emitted from the UV lamps 212 and 214, and other UV lamps disposed about the tunnel 206.

FIG. 2A illustrates a first wall 204 of the device 200 having a plurality of reflective units. A first reflective unit 218 is shown having a reflective back section 236, and reflective sections 238, 240, and 242 disposed about the back section 236 at an angle off normal with respect to the back section 236. The reflective unit 218 can also include a fourth reflective section (not shown). Three additional reflective units 219 are also shown.

At least one, and preferably, two UV lamps 212 and 214 are disposed within a recess formed by the reflective unit 218. In this manner, almost all of the light emitted by the UV lamps 212 and 214 can be directed toward equipment 110. Preferably, the UV lamps 212 and 214 are disposed perpendicularly to each other, although the lamps 212 and 214 could be disposed at non-right angles.

FIG. 2B illustrates a second wall 205 having a reflective unit 218 that includes a reflective back section 236 and reflective sections 238, 240, and 242 disposed about the back section 236 at an angle off normal with respect to the back section 236. At least one, and preferably, two UV lamps 212 and 214 are disposed within a recess formed by the reflective unit 218. In addition, device 200 can include upper UV lamps 256 that can direct additional UV light toward equipment 210. The second wall 205 can also include a third UV lamp 216 that is preferably disposed within a third reflective unit having a reflective back section and three or more reflective section coupled to the back section (not shown). With respect to the remaining numerals in FIGS. 2A-2B, the same considerations for like components with like numerals of FIG. 1 apply.

Figure 3:
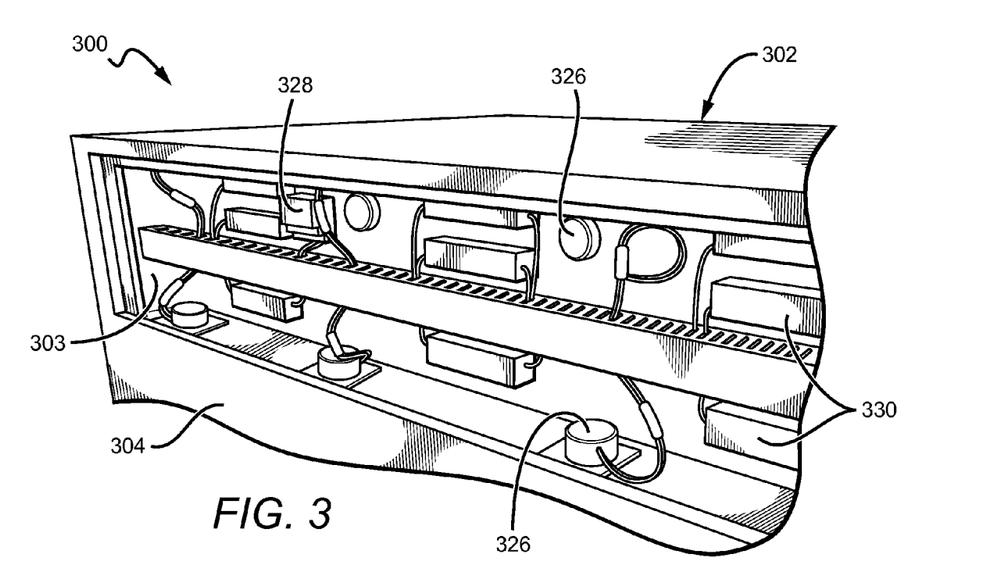
FIG. 3 is a side perspective view of a maintenance compartment of a device for disinfecting publicly-used equipment.

A side 304 of the housing 302 of a UV sanitizing device 300 is shown in FIG. 3. Side 304 can have a recess 303 that comprises some of the UV lamps' bases 326, and thereby advantageously allows easy access to the wiring and UV lamps for repair, removal, and replacement. Each of the UV lamp bases 326 can be coupled to an electronic ballast 330 to regulate the electrical current to the UV lamp. The device 300 can also have a controller 328 that can be used to cause the UV lamps to be turned on or off, as well regulate other electrical components of the device 300 including, for example, a door opener, one or more sensors, and so forth. Preferably, recess 303 includes a cover (not shown) that can hide the recess 303 and prevent unauthorized access to recess 303.

Figure 4:
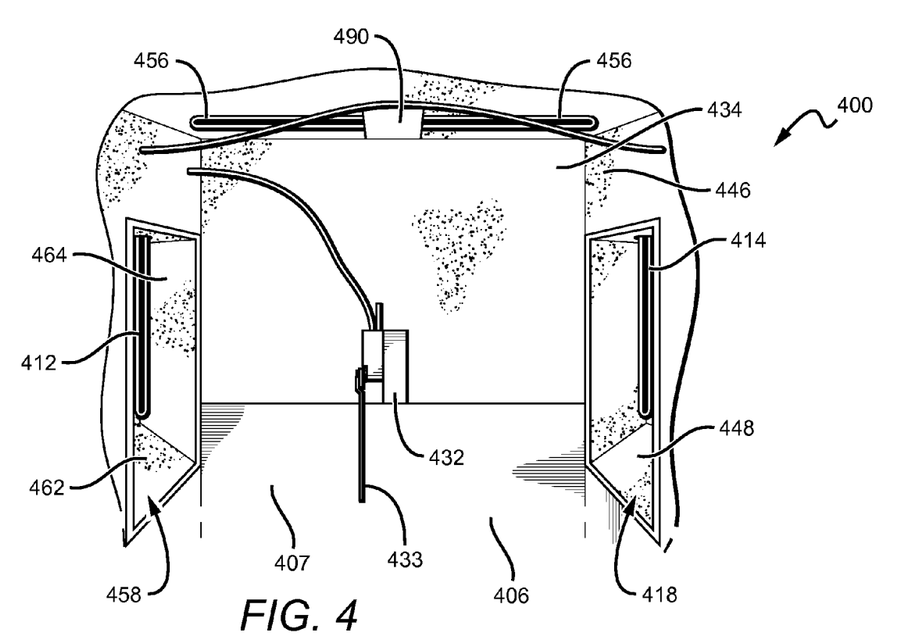
FIG. 4 is a inside view of a device for disinfecting publicly-used equipment.

In FIG. 4, device 400 includes a tunnel 406 having a back wall 434 and first and second walls 404 and 405. The back wall 434 can include a reflective sheet or lining that has a bumpy surface 446. Alternatively or additionally, at least a portion of the reflective sheet or lining could include a dimpled or other non-planar configuration, or a planar surface. The device 400 can also include a floor 407, or could instead utilize the ground or underlying surface as a floor.

The tunnel 406 can include an indicator 432 that determines whether or not a shopping cart or other piece of equipment is inserted within the tunnel 406 to thereby prevent undesired use of the device 400. As shown in FIG. 4, the indicator 432 can include a trigger 433, such that when a cart or other equipment is inserted within the tunnel 406, the trigger 433 will be depressed toward the back wall 434, and thereby complete or interrupt a circuit. This change in the circuit allows the device 400 to determine when equipment is properly inserted within the tunnel 406, and can thereby prevent activation of the UV lamps when equipment is improperly inserted, only partially inserted, or not at all inserted within the tunnel 406. This advantageously prevents the situation, for example, in which a child activates the device and then enters the tunnel instead of inserting a shopping cart, and is then exposed to UV radiation. The device 400 can include other configurations of indicators including, for example, motion, infrared and other sensors, one or more scales along the floor of the device 400, cameras, and combination(s) thereof.

In addition, all other commercially viable safety systems are contemplated. For example, device 400 could require a key or security code be entered prior to activation of the device 400. Additionally or alternatively, device 400 could have a controller (as shown in FIG. 3) coupled to one or more sensors such that when the sensors alert the controller to the presence of a person or other living creature, the controller shuts down the UV lamps. Such sensors could include for example, thermal or optical sensors. Passive safety systems could also be used including, for example, hanging light barriers at an opening of the tunnel 406.

The device 400 has a first wall 404 that can include a first reflective unit 418, and a second wall 405 that can include a second reflective unit 458. Each of the reflective units 418 and 458 can have at least three, and more preferably, at least four reflective sections. A first UV lamp 412 is disposed such that the first reflective unit 418 at least partially surrounds the first UV lamp 412. Similarly, a second UV lamp 414 is disposed such that the second reflective unit 458 at least partially surrounds the second UV lamp 414. Preferably, both of the first and second reflective units 418 and 458 are first surface reflectors, although second surface reflectors and other commercially suitable reflective surfaces could be used. Each of the reflective units 418 and 458 can have respective reflective sections 448 and 462 that extend along the floor and are angled of the floor by at least 10°.

UV lamps 456 can extend along the ceiling 490 and thereby provide additional sources and locations of UV light. With respect to the remaining numerals in FIG. 4, the same considerations for like components with like numerals of FIG. 1 apply.

Figure 5:
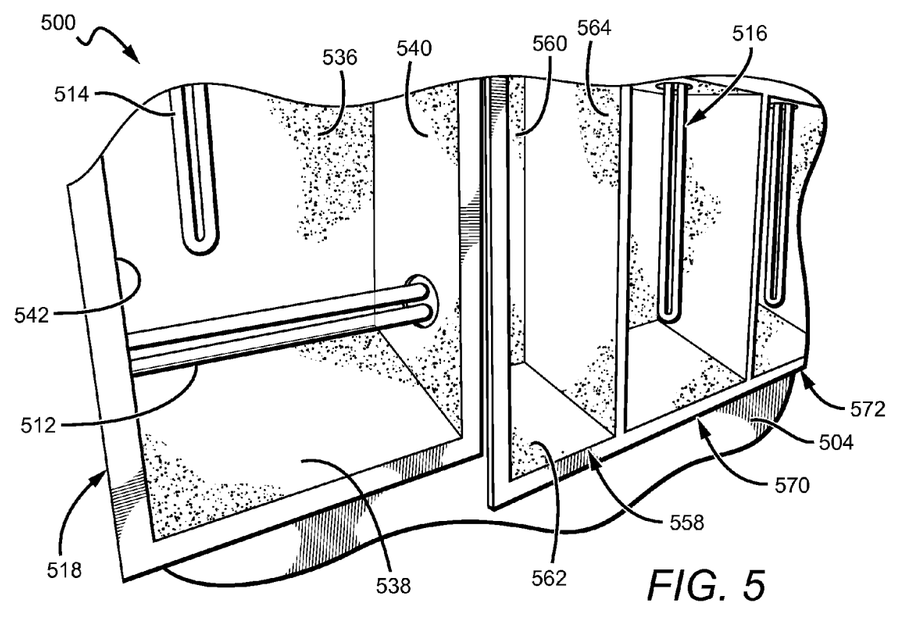
FIG. 5 is a perspective view of reflective units of a device.

FIG. 5 illustrates a first wall 504 of a device 500 that includes first and second reflective units 518 and 558. In addition, the device has third 570 and fourth reflective units 572. Depending on the size and dimension of device 500, and the type of equipment to be disinfected, the number of reflective units, and their configurations, can be varied. For example, to handle multiple carts at the same time, device 500 can be lengthened and include additional reflective units and UV lamps.

The first reflective unit 518 includes a reflective back section 536, and reflective sections 538, 540 and 542. At least one of the reflective sections 540 can include an aperture through which a first UV lamp 512 can be inserted. This is advantageous as the aperture allows the UV lamp 512 to be disposed within the reflective unit 518, and thereby position the UV lamp 512 with respect to the reflective unit 518 to reflect a larger portion of the UV light from UV lamp 512 toward equipment. A second UV lamp 514 can also be at least partially disposed within the reflective unit 518 to increase the intensity of the light. Although shown at a perpendicular orientation with respect to the first UV lamp 512, in other contemplated embodiments, the second UV lamp 514 could be parallel to, or at a non-right angle with respect to the first UV lamp 512.

The first wall 504 can also include a second reflective unit 558 that has a reflective back section 560, and reflective sections 562 and 564 that are disposed off normal with respect to the back section 560. Although not shown, the second reflective unit 558 can include third, and optionally, fourth reflective sections. The first wall 504 can further include a third UV lamp 516.

Figure 6:
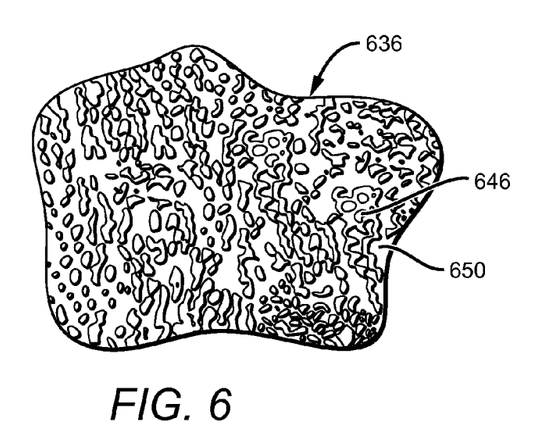
FIG. 6 is a close-up view of a reflective back section of a reflective unit.

In FIG. 6, a portion of a reflective back section 636 is shown having a bumpy surface 650 with a plurality of dimples 646.

Figure 7:
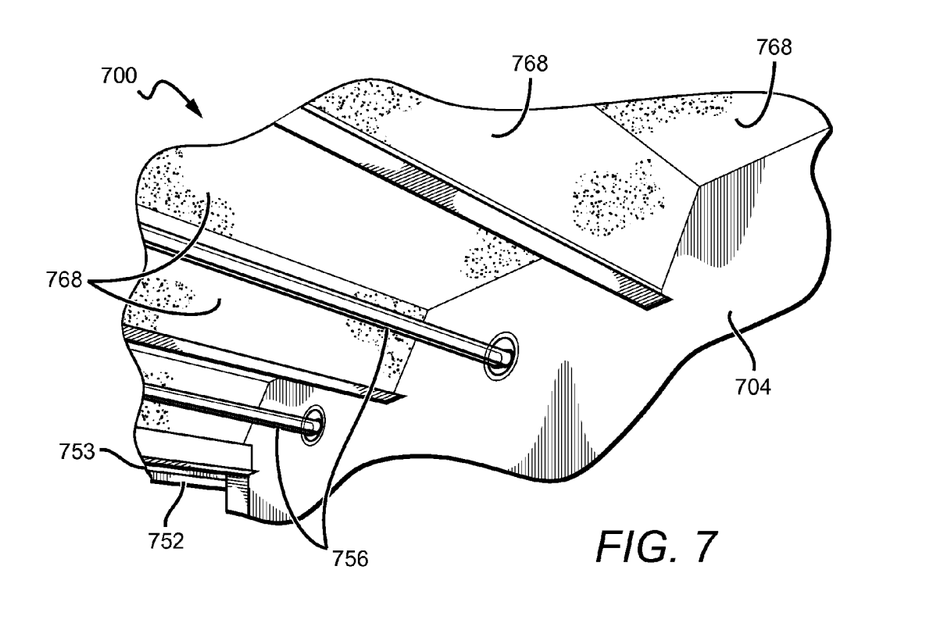
FIG. 7 is a perspective view of a ceiling of a device for disinfecting publicly-used equipment.

FIG. 7 illustrates a device 700 having a first wall 704 and a second wall (not shown), and a ceiling 790 that includes a plurality of reflective units 768. Each of the reflective units 768 includes a reflective back section 782, and at least two reflective sections 784 disposed off normal with respect to the back section 782. At least one UV lamp 756 can be disposed within each reflective unit 768, such that the UV lamp 756 is at least partially surrounded by at least one of the reflective units 768. Device 700 can also include opener 753 configured to electronically open and close door 752.

Figure 8A:
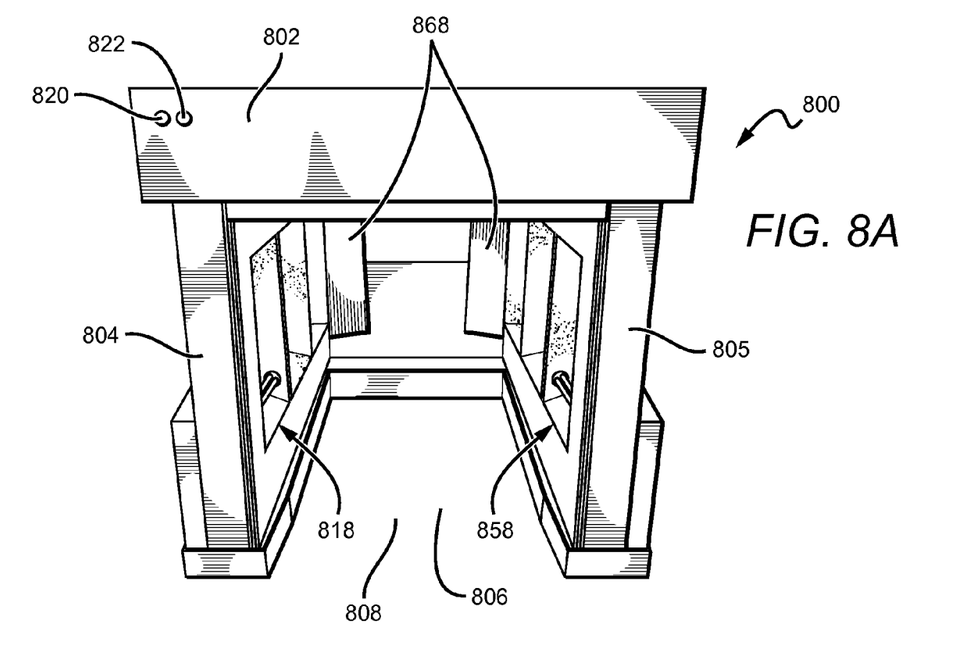
FIG. 8A is a front perspective view of an alternate embodiment of a device for disinfecting publicly-used equipment.
Figure 8B:
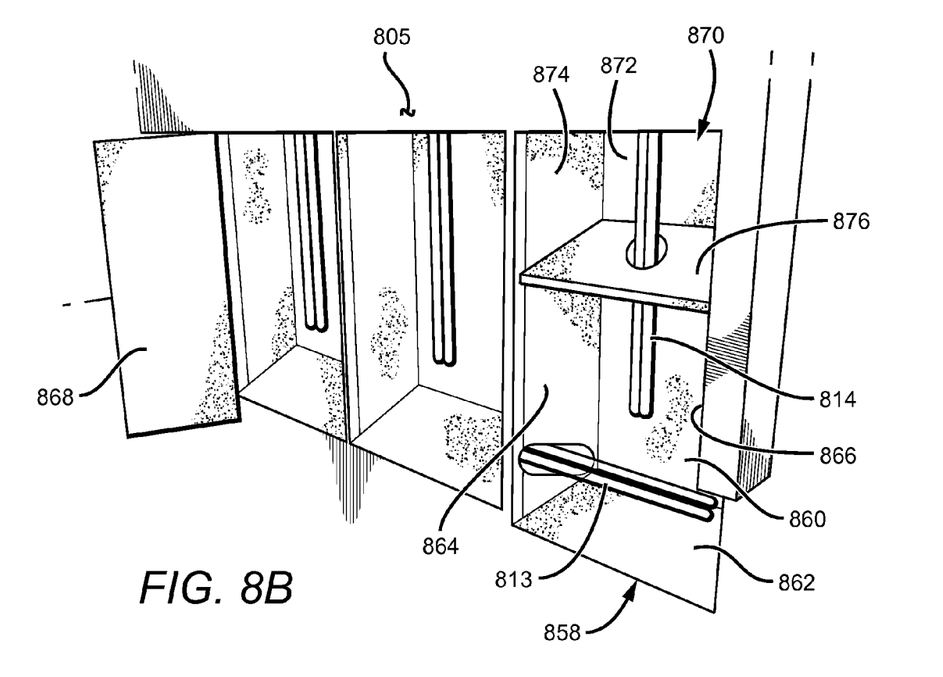
FIG. 8B is an inside view of the device of FIG. 8A.
Figures 8C, 10, 11A, 11B:
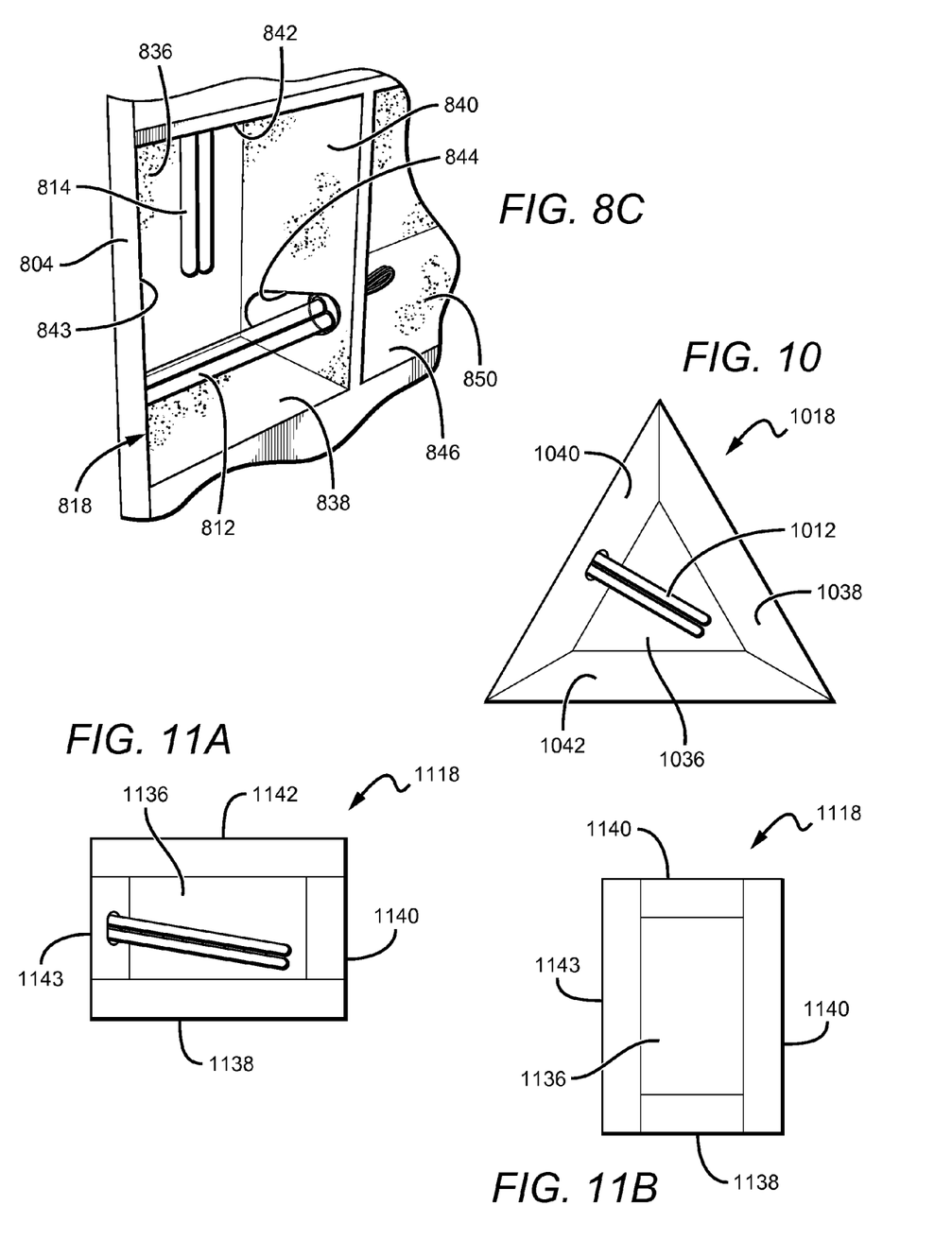
FIG. 8C is a close-up view of a reflective unit of the device of FIG. 8A.
FIG. 10 is a top view of a reflective unit having a triangular-shaped reflective back section.
FIGS. 11A-11B are top views of two additional embodiments of a reflective unit.

In FIGS. 8A-8C, yet another embodiment of a device 800 is shown having a housing 802 that includes first and second walls 804 and 805, and a ceiling. The housing 802 defines a tunnel 806. Reflective sections 868 can be disposed off normal with respect to each of the first and second walls 804 and 805.

The first wall 804 can include at least one reflective unit 818. As shown in FIG. 8C, the first reflective unit 818 can have four reflective sections 838, 840, 842 and 843, each of are disposed off normal with respect to a back section 836. At least one of the reflective sections 840 can include an aperture 844 though which a first UV lamp 812 can be inserted. The first wall 804 can include a second reflective unit 850 having an at least partially dimpled surface 846.

As shown in FIG. 8B, the second wall 805 can include a plurality of reflective units 858, 870, 890 and 892. Third reflective unit 858 can include three reflective sections 862, 864, and 866, and fourth reflective unit 870 can include three reflective sections 874, 876, and 878 and a reflective back section 872. A third UV lamp 814 can be inserted through an aperture in reflective section 876, and thereby be disposed in both reflective units 858 and 870. A fourth UV lamp 813 can be inserted through an aperture in reflective section 864 and thereby inserted within third reflective unit 858. The fourth UV lamp 813 can be inserted through an aperture in reflective section 876, and thereby be disposed within a cavity or recess formed by each of third and fourth reflective units 858 and 870. With respect to the remaining numerals in FIG. 8, the same considerations for like components with like numerals of FIG. 1 apply.

Figure 9:
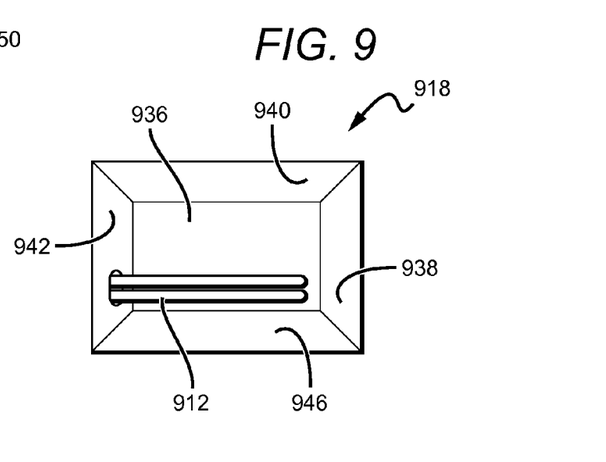
FIG. 9 is a top view of a reflective unit having a rectangular-shaped reflective back section.

FIG. 9 illustrates a reflective unit 918 that includes first, second, third, and fourth reflective sections 938, 940, 942, and 943, respectively, which are each disposed off normal with respect to a reflective back section 936. Intersections between adjacent reflective sections can be vertical or horizontal, or can be neither generally vertical nor generally horizontal. In this manner, the reflective unit 918 forms a cup-shape. A UV lamp 912 can be inserted through an aperture in the third reflective section 942.

FIG. 10 illustrates an alternative embodiment of a reflective unit 1018 having only three side or reflective sections 1038, 1040, and 1042. A UV lamp 1012 can be inserted through an aperture in reflective section 1040. The intersections between adjacent reflective sections are neither generally horizontal nor generally vertical.

In FIG. 11A, reflective unit 1118 includes a reflective back section 1136, and four reflective sections 1138, 1140, 1142, and 1143, which are each disposed off normal with respect to reflective back section 1136. Each of the adjacent reflective sections (e.g., sections 1140 and 1142) intersect at generally horizontal intersections. A UV lamp extends into the reflective unit 1118, and thereby extends along the wall at an angle off horizontal of at least 10°. In FIG. 11B, each of the adjacent reflective sections (e.g., sections 1140 and 1142) intersect at generally vertical intersections. With respect to the remaining numerals in FIG. 11B, the same considerations for like components with like numerals of FIG. 11A apply.

EXAMPLES

The following examples illustrate particular embodiments of the present inventive subject matter, and aids those of skill in the art in understanding and practicing the inventive subject matter. It is set forth for explanatory purposes only, and is not to be taken as limiting the present inventive subject matter in any manner.

Example #1

A device was tested having six UV bulbs disposed along the ceiling of the device. The UV bulbs produced UVc light at an intensity of 110 µWs/cm² at a distance of 1 meter. The tunnel had a height of 48 in, a depth of 29 in, and a width of 45 in.

When the UV lamps were illuminated about the tunnel, the following intensities were found using a radiometer:

| Portion of Shopping Cart Tested | UV Intensity (µWs/cm²) |
| --- | --- |
| Bottom of cart (17.5" from floor) facing up at 5' into unit | 208 |
| Bottom of cart (17.5" from floor) facing up at 6' into unit | 269 |
| Bottom of cart (17.5" from floor) facing side of unit at about 5' into unit | 37 |
| Handle bar of cart (42" from floor) facing up at 5' into unit | 128 |
| Handle bar of cart (42" from floor) facing up at 6' into unit | 694 |
| Top basket of cart (42" from floor) facing side of unit at about 5' into unit | 531 |

Based on the intensity measurements collected, inconsistency in the UV intensities at various areas of the shopping cart was discovered. In particular, the low intensity found at the bottom of the cart likely resulted from a lack of UV light being directed to that area. In this example, all six of the UV bulbs were located only along the top portion of the device, similar to prior art devices, and therefore, the device failed to provide a uniform UV intensity to the shopping cart.

Example #2

A device was tested in which UV bulbs were disposed along the walls and ceiling of the device. The UV bulbs produced UVc light at an intensity of 110 µWs/cm² at a distance of 1 meter. The tunnel had a height of 48 in, a depth of 29 in, and a width of 45 in.

When the UV lamps were illuminated about the tunnel, the following intensities were found using a radiometer:

| Portion of Shopping Cart Tested | UV Intensity (µWs/cm²) |
| --- | --- |
| Bottom of cart (17.5" from floor) facing up | About 650 |
| Bottom of cart (17.5" from floor) facing side of unit | About 950 |
| Handle bar of cart (42" from floor) facing up | About 1500 |
| Top basket of cart (42" from floor) facing up | About 2800 |

Based on the intensity measurements collected, it is expected that much of the cart can be substantially disinfected of many of the common microorganisms in less than seven seconds of exposure. It is expected that the entire cart could be disinfected of many of the common microorganisms in about ten seconds.

Example #3

A device was tested having UV lamps disposed throughout the device, and a plurality of reflective units were disposed along the walls in place of the reflective sheets in Example 2. The UV lamps produced UVc light at an intensity of 110 µWs/cm² at a distance of 1 meter. The tunnel had a height of 48 in, a depth of 29 in, and a width of 45 in. The device also included a door that closed the tunnel while the UV lamps were activated.

When the UV lamps were illuminated about the tunnel, the following intensities were found using a radiometer:

| Portion of Shopping Cart Tested | UV Intensity (µWs/cm²) |
| --- | --- |
| Handle bar of cart facing up | About 2200 |
| Handle bar of cart facing down | About 700 |
| Seat area bottom, facing up | About 2400 |
| Side of basket's interior, facing interior | About 2400 |
| Bottom of basket's interior, facing up | About 2000 |

Based on the intensity measurements collected, it appears that the intensity of the UV light was lowest at the bottom of the handle bar. However, it is likely that this value underestimated the actual intensity on this surface as a whole due to configuration limitations (e.g., the size and shape of sensor, and the small tangential area on round surfaces). It is expected that much of the cart could be substantially disinfected of many of the common microorganisms in about three seconds of exposure, and the entire cart, in about ten seconds or less.

To determine the actual percentage reduction of bacteria on the cart surfaces by the UV light, bacteria samples were attached to various areas of a shopping cart that was then subjected to UV light in the device for about 15 seconds. Overall, experimental data correlated with or exceeded theoretical calculations of percentage reduction in the tested organisms. Results of the experiment indicate reduction percentage rates for all bacteria tested of 97.34% to 100%, with only 2 out of 40 samples having a reduction percentage below 99%. The average reduction of sampled bacteria was 99.8%.

The tested organism with the highest dose level (e.g., hardest to kill) was salmonella typhimurium with a dose level of 15,200 µWs/cm². Even for locations with lower measured UV intensities, such as the handlebar facing down, experimental results indicate a greater than 99.5% reduction.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device for disinfecting publicly-used equipment, comprising:
   a housing defining a tunnel that has a wall, and an opening sized and dimensioned for insertion of the equipment;
   first and second walls, each wall having a plurality of reflective units, wherein each unit has a reflective back section and at least three reflective sections disposed off normal with respect to the back section; and
   a first UV light source extending along the first wall, and providing an intensity of at least 100 µW/cm² of UV light at 1 meter, to reflect UV light from the light source upwards or downwards within the tunnel.

2. The device of claim 1, wherein an intersection between at least two of the reflective sections is generally horizontal.

3. The device of claim 1, wherein an intersection between at least two of the reflective sections is generally vertical.

4. The device of claim 1, wherein an intersection between at least two of the reflective sections is neither generally vertical nor generally horizontal.

5. The device of claim 1, wherein at least one of the reflective sections of at least one reflective unit is a first surface reflector.

6. The device of claim 1, wherein at least one of the reflective sections of at least one reflective unit has a bumpy surface.

7. The device of claim 1, wherein the tunnel defines a pass-through space of at least 1.25 m in height.

8. The device of claim 1, wherein the tunnel is sized and dimensioned to receive a shopping cart.

9. The device of claim 1, wherein at least one of the reflective sections of at least one reflective unit has an at least partially dimpled surface.

10. The device of claim 1, wherein the first UV light source is disposed along the first wall, and angled off horizontal by at least 10°.

11. The device of claim 1, further comprising a second UV light source extending along the second wall.

12. The device of claim 1, further comprising a third UV light source extending along the first wall, and disposed perpendicularly with respect to the first UV light source.

13. The device of claim 1, further comprising a first UV reflector extending along a floor of the device, and that is angled off of the floor by at least 10°.

14. The device of claim 1, further comprising a door having a surface area of at least one square meter.

15. The device of claim 14, further comprising an opener configured to automatically open and close the door.

16. The device of claim 1, wherein the door comprises a window configured to filter the UV light.

* * * * *